US012570609B2

(12) United States Patent
Liu et al.

(10) Patent No.: US 12,570,609 B2
(45) Date of Patent: Mar. 10, 2026

(54) TRICYCLIC SULFONES AS ROR GAMMA MODULATORS

(71) Applicant: BRISTOL-MYERS SQUIBB COMPANY, Princeton, NJ (US)

(72) Inventors: Qingjie Liu, Newtown, PA (US); T.G. Murali Dhar, Newtown, PA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 663 days.

(21) Appl. No.: 17/794,661

(22) PCT Filed: Jan. 22, 2021

(86) PCT No.: PCT/US2021/014488
§ 371 (c)(1),
(2) Date: Jul. 22, 2022

(87) PCT Pub. No.: WO2021/150803
PCT Pub. Date: Jul. 29, 2021

(65) Prior Publication Data

US 2023/0093404 A1 Mar. 23, 2023

Related U.S. Application Data

(60) Provisional application No. 62/965,206, filed on Jan. 24, 2020.

(51) Int. Cl.
*C07D 221/16* (2006.01)
*C07D 409/12* (2006.01)

(52) U.S. Cl.
CPC ......... *C07D 221/16* (2013.01); *C07D 409/12* (2013.01)

(58) Field of Classification Search
CPC ............................ C07D 221/16; C07D 409/12
See application file for complete search history.

(56) References Cited

U.S. PATENT DOCUMENTS

| | | | | |
|---|---|---|---|---|
| 9,815,859 | B2 | 11/2017 | Duan et al. | |
| 10,435,369 | B2 * | 10/2019 | Marcoux .............. | C07D 263/20 |
| 2018/0127368 | A1 | 5/2018 | Marcoux et al. | |

FOREIGN PATENT DOCUMENTS

| | | | |
|---|---|---|---|
| WO | 2016179460 | A1 | 11/2016 |
| WO | 2018071314 | A1 | 4/2018 |
| WO | 2018071620 | A1 | 4/2018 |
| WO | 2019222438 | A1 | 11/2019 |

OTHER PUBLICATIONS

Kim, Molecules, 2021, vol. 26, 1854, 1-23. (Year: 2021).*
Lee, Sci China Life Sci, Aug. 2021, vol. 64 No 8, 1326-1335. (Year: 2021).*
Desai, Nature Portfolio, 2022, 12:8744, 1-15. (Year: 2022).*
Zeng, J Pharm Analysis, vol. 13, 2023, 545-562. (Year: 2023).*
Takeda, PLOS Genetics, May 2014, vol. 10, Issue 5, e1004331, 1-16. (Year: 2014).*
Santori, Cell Metabolism, 2015, vol. 21, 286-297. (Year: 2015).*
Pandya, J Med Chem, 2018, 61, 10976-10995. (Year: 2018).*
Liu, Q., "Azatricyclic Inverse Agonists of ROR y t That Demonstrate Efficacy in Models of Rheumatoid Arthritis and Psoriasis," ACS Medical Chemistry Letters, vol. 12, pp. 827-835 (2021).
Agache I., et al., "Increased serum IL-17 is an independent risk factor for severe asthma", Respiratory Medicine (2010) vol. 104, pp. 1131-1137.
Andre Elisabeth et al., "Disruption of retinoid-related orphan receptor β changes circadian behavior, causes retinal degeneration and leads to vacillans phenotype in mice", The EMBO Journal, (1998) vol. 17, No. 14, pp. 3867-3877.
Cua, Daniel J., et al. "Innate IL-17-producing cells: the sentinels of the immune system", Nature Reviews | Immunology (2010), vol. 10, pp. 479-489.
Dussault, Isabelle et al., "Orphan nuclear receptor RORα-deficient mice display the cerebellar defects of staggerer", Mechanisms of Development (1998), vol. 70, pp. 147-153.
Eberl, Gerard et al., "An essential function for the nuclear receptor RORγt in the generation of fetal lymphoid tissue inducer cells", Nature Immunology (2004), vol. 5, No. 1—pp. 64-73.
Fujino, S., et al. "Increased expression of interleukin 17 in inflammatory bowel disease", Gut (2003), vol. 52, pp. 65-70.
He, You-Wen et al., "RORγt, a Novel Isoform of an Orphan Receptor Negatively Regulates Fas Ligand Expression and IL-2 Production in T Cells" Immunity (1998), vol. 9, pp. 797-806.
Hirose, Takahisa et al., "RORγ: The third member of ROR/RZR orphan receptor subfamily that is highly expressed in skeletal muscle", Biochemical and Biophysical Research Communications, (1994), vol. 205, No. 3, pp. 1976-1983.
Hu, Yan et al., "The IL-17 pathway as a major therapeutic target in autoimmune diseases", Annals of The New York Academy of Sciences (2011), 1217, pp. 60-76.
Ivanov Ivaylo I. et al., "The Orphan Nuclear Receptor Rorγ Directs the Differentiation Program of Proinflammatory IL-17+ T Helper Cells", Cell (2006), vol. 126, pp. 1121-1133.

(Continued)

*Primary Examiner* — D Margaret M Seaman
(74) *Attorney, Agent, or Firm* — Robert Kajubi

(57) ABSTRACT

There are described RORγ modulators of the formula (I),

I

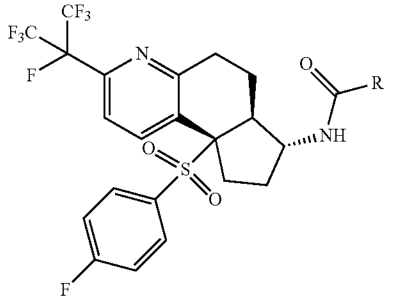

or stereoisomers, pharmaceutically acceptable salts thereof, wherein all substituents are defined herein.

4 Claims, No Drawings

(56) References Cited

OTHER PUBLICATIONS

Ivanov, Ivaylo I. et al., "Transcriptional regulation of Th17 cell differentiation", Seminars in Immunology (2007), vol. 19, pp. 409-417.
Jetten Anton M, "Retinoid-related orphan receptors (RORs): critical roles in development, immunity, circadian rhythm, and cellular metabolism", Nuclear Receptor Signaling (2009), vol. 7, pp. 1-32.
Kirkham Bruce W. et al., "Synovial Membrane Cytokine Expression Is Predictive of Joint Damage Progression in Rheumatoid Arthritis", Arthritis and Rheumatism (2006), vol. 54, No. 4, pp. 1122-1131.
Kotake, Shigeru et al., "IL-17 in synovial fluids from patients with rheumatoid arthritis is a potent stimulator of osteoclastogenesis", The Journal of Clinical Investigation (1999), vol. 103 (9), pp. 1345-1352.
Leonardi Craig, M.D. et al., "Anti-Interleukin-17 Monoclonal Antibody Ixekizumab in Chronic Plaque Psoriasis", The New England Journal of Medicine (2012), vol. 366; No. 13, pp. 1190-1199.
Leppkes Moritz et al., "RORγ-Expressing Th17 Cells Induce Murine Chronic Intestinal Inflammation via Redundant Effects of IL-17A and IL-17F", Gastroenterology (2009), vol. 136, pp. 257-267.
Lock, Christopher et al., "Gene-microarray analysis of multiple sclerosis lesions yields new targets validated in autoimmune encephalomyelitis", Nature Medicine (2002), vol. 8, No. 5, pp. 500-508.
Lowes Michelle A. et al., "Psoriasis Vulgaris Lesions Contain Discrete Populations of Th1 and Th17 T Cells", Journal of Investigative Dermatology (2008), vol. 128, pp. 1207-1211.
Maddur, Mohan S. et al., "Biology, Pathogenesis of Autoimmune and Inflammatory Diseases, and Therapeutic Strategies", The American Journal of Pathology (2012), vol. 181, No. 1, pp. 8-18.
Marks Benjamin R., et al. "Barrier immunity and IL-17", Seminars in Immunology (2009), vol. 21, pp. 164-171.
Ortiz, Maria Antonia et al., "TOR: A New Orphan Receptor Expressed in the Thymus That Can Modulate Retinoid and Thyroid Hormone Signals", Molecular Endocrinology (1995), vol. 9, No. 12, pp. 1679-1691.
Pantelyushin, Stanislav et al., Rorγt+ innate lymphocytes and γδ T cells initiate psoriasiform plaque formation in mice The Journal of Clinical Investigation (2012), vol. 122, No. 6, pp. 2252-2256.
Rautio, Jarkko, et. al., "The expanding role of prodrugs in contemporary drug design and development" Nature Reviews| Drug Discovery (2018), vol. 17, No. 8, pp. 559-587.
Seiderer Julia et al., "Role of the Novel Th17 Cytokine IL-17F in Inflammatory Bowel Disease (IBD): Upregulated Colonic IL-17F Expression in Active Crohn's Disease and Analysis of the IL17F p.His161Arg Polmorphism in IBD", Inflamm Bowel Dis (2008), vol. 14, No. 4, pp. 437-445.
Solt Laura A., et al., "Action of RORs and their ligands in (patho)physiology" Trends in Endocrinology and Metabolism (2012), vol. 23, No. 12, pp. 619-627.
Sun, Zuoming et al., "Requirement for RORγ in Thymocyte Survival and Lymphoid Organ Development", Science (2000), vol. 288, pp. 2369-2373.
Tilley, Stephen L., et al., "Retinoid-Related Orphan Receptor γ Controls Immunoglobulin Production and Th1/Th2 Cytokine Balance in the Adaptive Immune Response to Allergen", The Journal of Immunology (2007), vol. 178, pp. 3208-3218.
Tzartos, John S., et al., "Interleukin-17 Production in Central Nervous System-Infiltrating T Cells and Glial Cells Is Associated with Active Disease in Multiple Sclerosis", The American Journal of Pathology, (2008), vol. 172, No. 1, pp. 146-155.
Wong C.K. et al., "Proinflammatory cytokines (IL-17, IL-6, IL-18 and IL-12) and Th cytokines (IFN-γ, IL-4, IL-10 and IL-13) in patients with allergic asthma", Clin Exp Immunol (2001), vol. 125, pp. 177-183.
Wuts, Peter G.M., et al., Protecting Groups in Organic Synthesis, 4th Edition, Wiley (2007)).
Yang, Xuexian O., et al., "T Helper 17 Lineage Differentiation Is Programmed by Orphan Nuclear Receptors RORα and RORγ", Immunity (2008), vol. 28, pp. 29-39.

* cited by examiner

TRICYCLIC SULFONES AS ROR GAMMA MODULATORS

CROSS-REFERENCE TO RELATED APPLICATIONS

This application is a 371 International Application of PCT/US2021/014488, filed Jan. 22, 2021, which claims the priority benefit of U.S. Provisional Application No. 62/965,206, filed Jan. 24, 2020, the disclosure of which is incorporated herein by reference in its entirety.

FIELD OF THE INVENTION

This invention relates to modulators of the retinoid-related orphan receptor RORγ and methods for using said modulators. The compounds described herein can be particularly useful for treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis, systemic lupus erythematosus, lupus nephritis, Sjögren's syndrome and multiple sclerosis.

BACKGROUND OF THE INVENTION

The retinoid-related orphan receptors, RORα, RORβ, and RORγ, play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of Formula (I), (I)

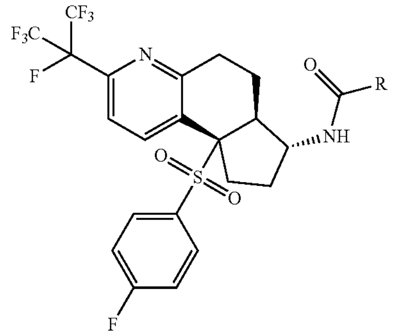

or pharmaceutically acceptable salts thereof, wherein R is

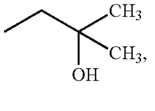
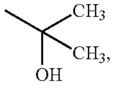
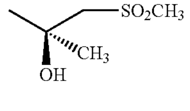
,

-continued

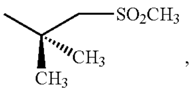
,
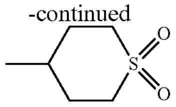
or
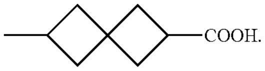

The invention includes tautomers, solvates, or prodrugs thereof.

In another aspect, the invention comprises the compound of Formula (II)

(II)

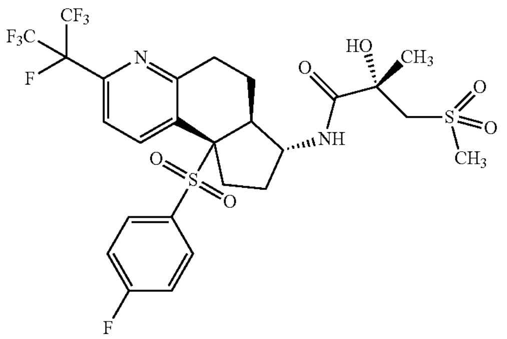

which is (S)—N-((6aS,7R,9aS)-9a-((4-fluorophenyl)sulfonyl)-3-(perfluoropropan-2-yl)-6,6a,7,8,9,9a-hexahydro-5H-cyclopenta[f]quinolin-7-yl)-2-hydroxy-2-methyl-3-(methylsulfonyl)propanamide.

In another aspect, the invention comprises pharmaceutical compositions comprising the compound according to Formula (II) or a pharmaceutically acceptable salt, as described herein, and a pharmaceutically acceptable carrier, excipient, or diluent.

In another aspect, the invention comprises pharmaceutical compositions comprising the compound according to Formula (I) or a pharmaceutically acceptable salt, as described herein, and a pharmaceutically acceptable carrier, excipient, or diluent.

In another aspect, the invention comprises methods for modulating RORγ in a cell comprising contacting the cell with an effective amount of the compound according to formula (I) or a pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of the compound according to formula (I) or a pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of the compound according to formula (I), or a pharmaceutically acceptable salt or pharmaceutical composition as described herein.

DETAILED DESCRIPTION OF THE INVENTION

In one aspect, the invention comprises a compound of Formula (I), (I)

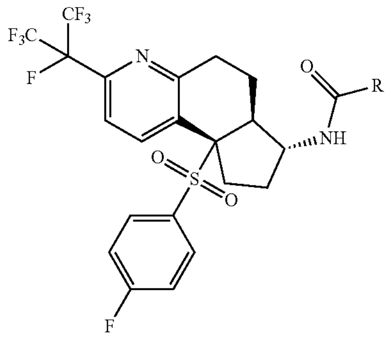

or a pharmaceutically acceptable salt or solvate thereof.

In another aspect, the invention comprises the compound of Formula (II)

(II)

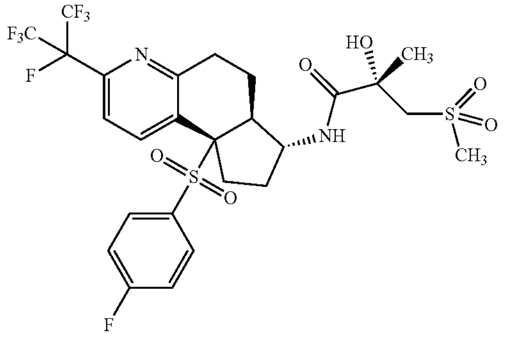

which is (S)—N-((6aS,7R,9aS)-9a-((4-fluorophenyl)sulfonyl)-3-(perfluoropropan-2-yl)-6,6a,7,8,9,9a-hexahydro-5H-cyclopenta[f]quinolin-7-yl)-2-hydroxy-2-methyl-3-(methylsulfonyl)propanamide.

In one embodiment, the invention provides a pharmaceutical composition, comprising a pharmaceutically acceptable carrier and a therapeutically effective amount of a compound of the invention or a pharmaceutically acceptable salt or solvate thereof.

In another embodiment, the invention provides a process for making a compound of the invention or a pharmaceutically acceptable salt or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis, systemic lupus erythematosus, lupus nephritis, Sjögren's syndrome and multiple sclerosis.

The following are definitions of terms used in this specification and appended claims. The initial definition provided for a group or term herein applies to that group or term throughout the specification and claims, individually or as part of another group, unless otherwise indicated.

A compound of formula I which contains a carboxylic acid may exist in a free form (with no ionization) or can form salts which are also within the scope of this invention. Unless otherwise indicated, reference to an inventive compound is understood to include reference to the free form and to salts thereof. The term "salt(s)" denotes basic salt(s) formed with inorganic and/or organic bases. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus are contemplated within the scope of the invention. Salts of the compound of formula I may be formed, for example, by reacting a compound of the formula I with an amount of base, such as an equivalent amount, in a medium such as one in which the salt precipitates or in an aqueous medium followed by lyophilization.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compound wherein the parent compound is modified by making base salts thereof. Examples of pharmaceutically acceptable salts include, but are not limited to, alkali or organic salts of the carboxylic acid. The pharmaceutically acceptable salts include the conventional non-toxic salts or the quaternary ammonium salts of the parent compound formed, for example, from non-toxic inorganic or organic bases.

The pharmaceutically acceptable salts of the present invention can be synthesized from the parent compound which contains an acidic moiety, by conventional chemical methods. Generally, such salts can be prepared by reacting the free acid form of the compound with a stoichiometric amount of the appropriate base in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, PA (1990), the disclosure of which is hereby incorporated by reference.

Prodrugs and solvates of the inventive compound are also contemplated. The term "prodrug" denotes a compound which, upon administration to a subject, undergoes chemical conversion by metabolic or chemical processes to yield the compound of formula I, and/or a salt and/or solvate thereof. Any compound that will be converted in vivo to provide the bioactive agent (i.e., a compound for formula I) is a prodrug within the scope and spirit of the invention. For example, a carboxylic acid group of a compound of formula I can form physiologically hydrolyzable esters which serve as prodrugs by being hydrolyzed in the body to yield the compound of formula I per se. Such prodrugs are preferably administered orally since hydrolysis in many instances occurs principally under the influence of digestive enzymes. Parenteral administration may be used where the ester per se is active, or in those instances where hydrolysis occurs in the blood. Examples of physiologically hydrolyzable esters of a carboxylic acid compound of formula I include $C_{1-6}$ alkylbenzyl, 4-methoxybenzyl, indanyl, phthalyl, methoxymethyl, $C_{1-6}$ alkanoyloxy-$C_{1-6}$ alkyl, e.g., acetoxymethyl, pivaloyloxymethyl or propionyloxymethyl, $C_{1-6}$ alkoxycarbonyloxy-$C_{1-6}$ alkyl, e.g., methoxycarbonyloxymethyl or ethoxycarbonyloxymethyl, glycyloxymethyl, phenylglycyloxymethyl, (5-methyl oxo-1,3-dioxolen-4-yl)-methyl and other well-known physiologically hydrolyzable esters used, for example, in the penicillin and cephalosporin arts. Such esters may be prepared by conventional techniques known in the art.

Various forms of prodrugs are well known in the art and are described in Rautio, J. et al., *Nature Review Drug Discovery,* 17, 559-587 (2018).

Another aspect of the invention is a pharmaceutical composition including a compound of Formula I, or a pharmaceutical salt or solvate thereof, as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablets, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, a compound described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compound and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutically acceptable salts.

The therapeutic dosage of the compound can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, a compound described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the biological efficacy of the compound, formulation of the excipient, and its route of administration. Effective doses can be extrapolated from dose-response curves derived from in vitro or animal model test systems.

A compound of the present invention is useful to prevent, diagnose, and treat various medical disorders in humans or animals. The compound is used to inhibit or reduce one or more activities associated with RORγ receptors, relative to RORγ receptors in the absence of the same compound. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of a compound of formula (I), or a pharmaceutically acceptable salt, solvate, or pharmaceutical composition as described herein. See, e.g., L. A. Solt et al., "Action of RORs and their ligands in (patho)physiology," *Trends Endocrinol. Metab.* 2012, 23 (12): 619-627; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases, Sjögren's syndrome and systemic lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis.

In other embodiments, the disease or disorder is multiple sclerosis.

In other embodiments, the disease or disorder is ankylosing spondylitis.

In other embodiments, the disease or disorder is inflammatory bowel disease.

In other embodiments, the disease or disorder is lupus.

In other embodiments, the disease or disorder is Sjögren's syndrome.

In other embodiments, the disease or disorder is psoriasis.

In other embodiments, the disease or disorder is psoriatic arthritis.

In other embodiments, the disease or disorder is graft-vs.-host disease (GVHD).

In other embodiments, the disease or disorder is autoimmune uveitis.

In other embodiments, the disease or disorder is obesity and/or insulin resistance.

In other embodiments, the disease or disorder is melanoma.

In certain aspects, the medical disorder being diagnosed, treated, or prevented by use of a presently disclosed compound can be, for example, an autoimmune disorder. In other embodiments, the disorder being diagnosed, treated or prevented by use of a presently disclosed compound can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Methods of Preparation

The compounds of the present invention may be synthesized by many methods available to those skilled in the art of organic chemistry. Methods for preparing intermediates and compounds of the present invention are described in the examples below. These methods are illustrative and are not meant to limit the possible techniques one skilled in the art may use to prepare the intermediates and compounds disclosed herein. Different methods to prepare the compounds of the present invention will be evident to those skilled in the art. Frequently chemists skilled in the art of synthesis may devise alternative preparations which may be desirable based on one or more considerations such as shorter reaction time, less expensive starting materials or reagents, ease of operation or isolation, improved yield, suitability to catalysis, avoidance of toxic reagents, accessibility of specialized instrumentation, decreased number of linear steps, etc.

Preparation of homochiral examples may be carried out by techniques known to one skilled in the art. For example, homochiral compounds may be prepared by separation of racemic products or diastereomers by, for example, chiral phase preparative HPLC. Alternatively, the example compounds may be prepared by methods known to give enantiomerically or diastereomerically enriched products.

The reactions and techniques described below to prepare the intermediates and compounds of the present invention are performed in solvents appropriate to the reagents and materials employed and are suitable for the transformations being effected. It is to be understood that all reaction conditions, including choice of solvent, reaction atmosphere, reaction temperature, duration of the experiment and work up procedures, are chosen to be conditions suitable for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common Intermediates are generally useful for the preparation of more than one Example and are identified sequentially by the Intermediate number and step in which they were prepared (e.g., Intermediate 1, Step A), or by the Intermediate number only where the compound is the title compound. Compounds of the Examples are identified by the Example number and step in which they were prepared (e.g., Example 1, Step A) if the compound is an intermediate, or by the Example number only where the compound is the title compound of the Example. Frequently chemists skilled in the art of synthesis may devise alternative preparations which may be desirable based on one or more considerations such as shorter reaction time, less expensive starting materials, ease of operation or isolation, improved yield, suitability to catalysis, avoidance of toxic reagents, accessibility of specialized instrumentation, decreased number of linear steps, etc. Starting materials and intermediates for which no preparation is explicitly shown are available commercially or are known in the literature.

Drying of organic solutions to remove residual water was done by allowing to stand over anhydrous sodium sulfate or anhydrous magnesium sulfate, followed by decantation or filtration. Solvent removal was performed by concentration under reduced pressure. Column chromatography was generally performed with pre-packed silica gel cartridges using a CombiFlash® automated chromatography apparatus (Teledyne Isco), eluting with the solvent or solvent mixture indicated.

Analytical HPLC was performed using the following conditions: column—XBridge™ $C_{18}$, 2.1×50 mm, 1.7 μm (Waters Corp.); temperature 50° C.; mobile phase A—5:95 MeCN-water with 0.1% TFA; mobile phase B—95:5 MeCN-water with 0.1% TFA; gradient 0 to 100% B over 3 min, then 0.75 min at 100% B; flow rate 1 mL/min; detection by MS and UV (220 nm).

Preparative HPLC was performed using the following conditions: column—XBridge™ $C_{18}$ 19×200 mm, 5 μm (Waters Corp.); mobile phase A—5:95 MeCN-water with 10 mM ammonium acetate; mobile phase B—95:5 MeCN-water with 10 mM ammonium acetate; gradient: increasing B, then isocratic; flow rate 20 mL/min. Chiral super-critical fluid chromatographic separation of enantiomers or diastereomers was performed using conditions described for the individual cases. Mass spectral data were obtained by liquid chromatography mass spectroscopy using electrospray ionization.

Chemical names were determined using ChemBioDraw Ultra, version 16.0.1.4 (PerkinElmer Inc.).

The following abbreviations are used:

| ABBREVIATION | NAME |
|---|---|
| DCE | 1,2-dichloroethane |
| DCM | dichloromethane |
| DIEA | diisopropylethylamine (Hünig's base) |
| DMF | N,N-dimethylformamide |
| DMSO | dimethyl sulfoxide |
| EtOAc | ethyl acetate |
| h | hours |
| HATU | O-(7-azabenzotriazol-1-yl)-1,1,3,3-tetramethyluronium hexafluorophosphate |
| HPLC | high performance liquid chromatography |
| LCMS | liquid chromatography - mass spectrometry |
| mCPBA | m-chloroperoxybenzoic acid |
| MeCN | acetonitrile |
| MeOH | methanol |
| min | minutes |
| rt | room temperature |
| SFC | super-critical fluid chromatography |
| TFA | trifluoroacetic acid |
| THF | tetrahydrofuran |
| $t_R$ | chromatographic retention time |

Intermediate 1

(6aS,7R,9aS)-9a-((4-fluorophenyl)sulfonyl)-3-(perfluoropropan-2-yl)-6,6a,7,8,9,9a-hexahydro-5H-cyclopenta[f]quinolin-7-amine, HCl salt

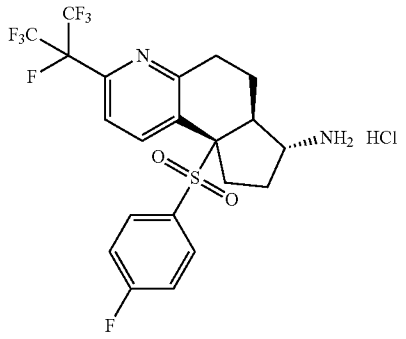 [SMILES: N[C@@H]1CC[C@@]2(S(=O)(=O)c3ccc(F)cc3)c3ccc(C(F)(C(F)(F)F)C(F)(F)F)nc3CC[C@@H]12 ; Cl]

Step A: 7,8-dihydroquinoline-2,5(1H,6H)-dione

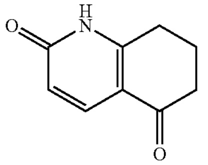 [SMILES: O=C1CCCc2[nH]c(=O)ccc21]

A mixture of 3-amino-2-cyclohexen-1-one (12.0 g, 108 mmol) and ethyl propiolate (14.6 mL, 144 mmol) was heated to 100° C. overnight. The temperature was then increased to 170° C. for 2 h, then cooled. The dark brown mixture was treated dropwise with MeOH (35 mL) over 20 min, gradually forming a suspension which was stirred at 70° C. for 2 h. The mixture was cooled to 0° C. and stirred for 1 h. The precipitate was collected by filtration, washed with a 2:1 mixture of heptane and DCM (30 mL), then with MeOH (10 mL), and air dried to provide 7,8-dihydroquinoline-2,5(1H,6H)-dione as a brown-yellow solid (4.4 g). LCMS m/z 163.9 $(M+H)^+$. $^1H$ NMR (499 MHz, DMSO-$d_6$) δ 12.08 (br s, 1H), 7.77 (d, J=9.5 Hz, 1H), 6.24 (d, J=9.5 Hz, 1H), 2.79 (t, J=6.2 Hz, 2H), 2.44-2.40 (m, 2H), 2.00 (quin, J=6.4 Hz, 2H).

Step B: 2-((2,6-dichlorobenzyl)oxy)-7,8-dihydroquinolin-5(6H)-one

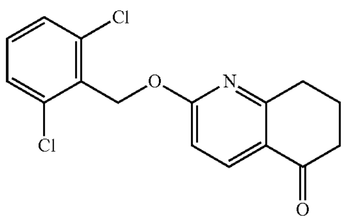 [SMILES: O=C1CCCc2nc(OCc3c(Cl)cccc3Cl)ccc21]

A mixture of 7,8-dihydroquinoline-2,5(1H,6H)-dione (8.65 g, 53.0 mmol), 2-(bromomethyl)-1,3-dichlorobenzene (15.3 g, 63.6 mmol), and $Cs_2CO_3$ (17.3 g, 53.0 mmol) in MeCN (200 ml) was stirred at rt for 22 h. The precipitate was removed by filtration and the filtrate was concentrated. The residue was partitioned between EtOAc and water, and the organic phase was washed with brine, dried over $MgSO_4$, and concentrated. The residue was purified by column chromatography on silica gel (220 g), eluting with EtOAc-hexanes (gradient from 5-10%), to provide 2-((2,6-dichlorobenzyl)oxy)-7,8-dihydroquinolin-5(6H)-one as a white solid (14.5 g). LCMS m/z 322.0, 324.0 $(M+H)^+$. $^1H$ NMR (499 MHz, $CDCl_3$) δ 8.19 (d, J=8.6 Hz, 1H), 7.39-7.36 (m, 2H), 7.28-7.24 (m, 1H), 6.69 (d, J=8.6 Hz, 1H), 5.68 (s, 2H), 3.08 (t, J=6.2 Hz, 2H), 2.69-2.60 (m, 2H), 2.19 (quin, J=6.4 Hz, 2H).

Step C: 2-((2,6-dichlorobenzyl)oxy)-7,8-dihydroquinolin-5-yl trifluoromethanesulfonate

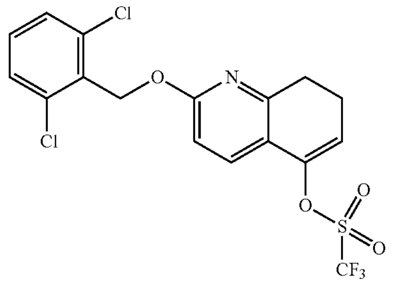 [SMILES: O=S(=O)(OC1=CCCc2nc(OCc3c(Cl)cccc3Cl)ccc21)C(F)(F)F]

A solution of 2-((2,6-dichlorobenzyl)oxy)-7,8-dihydroquinolin-5(6H)-one (8.24 g, 25.6 mmol) and N,N-bis(trifluoromethylsulfonyl)aniline (11.9 g, 33.2 mmol) in anhydrous THF was cooled to −78° C. and was treated with 1 M potassium bis(trimethylsilyl)amide (1.0 M in toluene; 34.5 mL, 34.5 mmol) over about 10 min. After stirring for 80 min, the mixture was treated with water and warmed to rt. Saturated aqueous $NaHCO_3$ was added and the mixture was extracted with ether. The organic phase was washed with brine, dried over $Na_2SO_4$ and concentrated. The residue was purified by column chromatography on silica gel (220 g), eluting with EtOAc-hexanes (gradient from 0-5%), to provide 2-((2,6-dichlorobenzyl)oxy)-7,8-dihydroquinolin-5-yl trifluoromethanesulfonate as a colorless syrup (7.29 g). LCMS m/z 454.0, 456.0 $(M+H)^+$. $^1H$ NMR (499 MHz, $CDCl_3$) δ 7.54 (d, J=8.5 Hz, 1H), 7.39 (d, J=8.1 Hz, 2H), 7.27-7.21 (m, 1H), 6.68 (d, J=8.5 Hz, 1H), 5.94 (t, J=4.8 Hz, 1H), 5.62 (s, 2H), 3.04 (t, J=8.6 Hz, 2H), 2.63 (td, J=8.6, 4.8 Hz, 2H). An additional portion of impure 2-((2,6-dichlorobenzyl)oxy)-7,8-dihydroquinolin-5-yl trifluoromethanesulfonate was also isolated as a separate colorless syrup (4.39 g).

Step D: 2-((2,6-dichlorobenzyl)oxy)-5-((4-fluoro-phenyl)thio)-7,8-dihydroquinoline

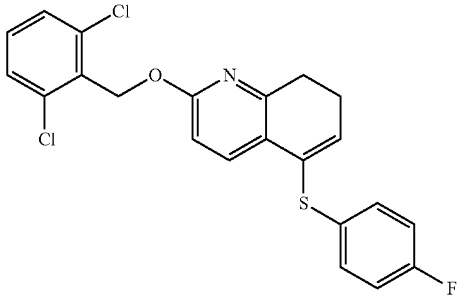 [SMILES: Fc1ccc(SC2=CCCc3nc(OCc4c(Cl)cccc4Cl)ccc32)cc1]

A mixture of 2-((2,6-dichlorobenzyl)oxy)-7,8-dihydro-quinolin-5-yl trifluoromethanesulfonate (20.2 g, 44.5 mmol), 4,5-bis(diphenylphosphino)-9,9-dimethylxanthine (1.29 g, 2.22 mmol), tris(dibenzylideneacetone)dipalladium (0) (1.63 g, 1.78 mmol) and DMA (14.0 mL, 80 mmol) in 1,4-dioxane (127 mL) in a pressure flask was treated with 4-fluorobenzenethiol (8.5 mL, 80 mmol). The mixture was purged with nitrogen for 5 min, and the vessel was sealed under a nitrogen atmosphere and heated at 115° C. for 3 h. The mixture was cooled to rt, filtered through a Celite pad, and the solids were washed with ether. The filtrate was partitioned between saturated aqueous $NaHCO_3$ and ether. The organic phase was washed with brine, dried over $MgSO_4$ and concentrated. The residue was purified by column chromatography on silica gel (750 g), eluting with EtOAc-hexanes (gradient from 0-25%), to provide 2-((2,6-dichlorobenzyl)oxy)-5-((4-fluorophenyl)thio)-7,8-dihydro-quinoline as a light yellow syrup (16.0 g). LCMS m/z 432.0, 434.0 $(M+H)^+$. $^1H$ NMR (499 MHz, $CDCl_3$) δ 7.65 (d, J=8.5 Hz, 1H), 7.36 (d, J=8.0 Hz, 2H), 7.26-7.21 (m, 3H), 6.96 (t, J=8.7 Hz, 2H), 6.52 (d, J=8.5 Hz, 1H), 6.40 (t, J=4.6 Hz, 1H), 5.58 (s, 2H), 3.01 (t, J=8.4 Hz, 2H), 2.57 (td, J=8.4, 4.6 Hz, 2H).

Step E: 2-((2,6-dichlorobenzyl)oxy)-5-((4-fluoro-phenyl)sulfonyl)-7,8-dihydroquinoline

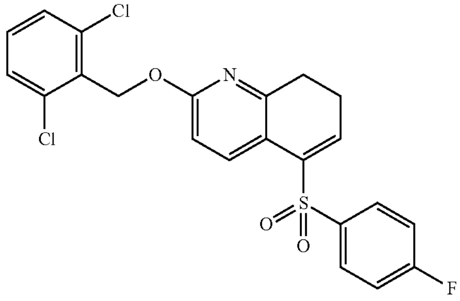 [SMILES: O=S(=O)(C1=CCCc2nc(OCc3c(Cl)cccc3Cl)ccc21)c1ccc(F)cc1]

A solution of 2-((2,6-dichlorobenzyl)oxy)-5-((4-fluoro-phenyl)thio)-7,8-dihydroquinoline (16.0 g, 37.0 mmol) in DCM (463 mL) was cooled on an ice-water bath and treated portionwise with mCPBA (19.9 g, 89.0 mmol). The resulting suspension was stirred at 0° C. for 2 h, then was filtered and the collected solid was washed with DCM. The filtrate was treated with saturated aqueous $NaHCO_3$ and the mixture was stirred for 10 min. The organic phase was separated, washed sequentially with saturated aqueous $NaHCO_3$, 10% aqueous $Na_2S_2O_3$, and brine, dried over $MgSO_4$ and concentrated. The residue was dried under vacuum to provide 2-((2,6-dichlorobenzyl)oxy)-5-((4-fluorophenyl)sulfonyl)-7,8-dihy-droquinoline as an off-white solid (16.3 g). LCMS m/z 464.2, 466.1 $(M+H)^+$. $^1H$ NMR (499 MHz, $CDCl_3$) δ 8.08 (d, J=8.7 Hz, 1H), 7.98-7.89 (m, 2H), 7.37-7.34 (m, 2H), 7.31 (t, J=4.9 Hz, 1H), 7.26-7.22 (m, 1H), 7.18 (t, J=8.6 Hz, 2H), 6.58 (d, J=8.7 Hz, 1H), 5.56 (s, 2H), 3.00-2.86 (m, 2H), 2.67 (td, J=8.4, 4.9 Hz, 2H).

Step F: ethyl 3-((2,6-dichlorobenzyl)oxy)-9a-((4-fluorophenyl)sulfonyl)-6,6a,7,8,9,9a-hexahydro-5H-cyclopenta[f]quinoline-7-carboxylate (mixture of diastereomers)

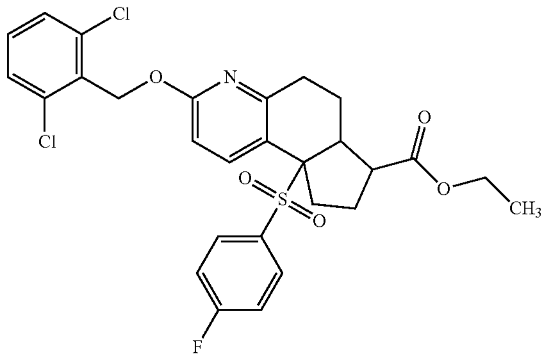 [SMILES: CCOC(=O)C1CCC2(S(=O)(=O)c3ccc(F)cc3)c3ccc(OCc4c(Cl)cccc4Cl)nc3CCC12]

A solution of 2-((2,6-dichlorobenzyl)oxy)-5-((4-fluoro-phenyl)sulfonyl)-7,8-dihydroquinoline (17.1 g, 36.8 mmol) and ethyl 4-chlorobutanoate (21.1 mL, 147 mmol) in THF (184 mL) was cooled to −78° C. and treated over 30 min with lithium bis(trimethylsilyl)amide (1.0 M in THF; 147 mL, 147 mmol). The resulting mixture was stirred at −78° C. for 2 h, then slowly allowed to warm to rt overnight. After 18 h, the mixture was cooled to 0° C. and treated with saturated aqueous $NH_4Cl$. The mixture was concentrated under vacuum to about half volume, then partitioned between ether and saturated aqueous $NH_4Cl$. The organic phase was washed sequentially with saturated aqueous $NH_4Cl$ and brine, dried over $MgSO_4$, and concentrated. The resulting light brown syrup was triturated with ether, forming a solid. The suspension was stirred at 0° C. for 30 min, and the solid was collected by filtration, washed twice with cold ether, and dried under vacuum to provide a mixture of diastereomers of ethyl 3-((2,6-dichlorobenzyl)oxy)-9a-((4-fluorophenyl)sulfonyl)-6,6a,7,8,9,9a-hexahydro-5H-cyclo-penta[f]quinoline-7-carboxylate as a light brown solid (7.83 g). LCMS m/z 578.5, 580.5 $(M+H)^+$. $^1H$ NMR (499 MHz, $CDCl_3$) δ 7.68 (d, J=8.6 Hz, 1H), 7.41-7.34 (m, 4H), 7.29-7.23 (m, 1H), 7.05 (t, J=8.6 Hz, 2H), 6.67 (d, J=8.7 Hz, 1H), 5.64-5.49 (m, 2H), 4.23 (q, J=7.2 Hz, 2H), 3.28 (td, J=8.7, 5.9 Hz, 1H), 3.18 (ddd, J=13.9, 7.6, 3.6 Hz, 1H), 2.73-2.65 (m, 1H), 2.58 (dt, J=16.9, 5.2 Hz, 1H), 2.37 (dtd, J=12.5, 9.8, 7.6 Hz, 1H), 2.16 (ddd, J=13.9, 10.0, 7.2 Hz, 1H), 2.11-2.01 (m, 2H), 1.96 (ddd, J=16.9, 9.8, 4.4 Hz, 1H), 1.45 (dtd, J=13.8, 9.3, 4.6 Hz, 1H), 1.32 (t, J=7.2 Hz, 3H). The filtrate was concentrated and the residue was purified by column chromatography on silica gel (330 g), eluting with EtOAc-hexanes (gradient from 5-25%), to provide additional ethyl 3-((2,6-dichlorobenzyl)oxy)-9a-((4-fluorophenyl)sulfonyl)-6,6a,7,8,9,9a-hexahydro-5H-cyclopenta[f]quinoline-7-carboxylate as an off-white glassy solid (7.68 g) of slightly reduced purity.

Step G: ethyl 9a-((4-fluorophenyl)sulfonyl)-3-hydroxy-6,6a,7,8,9,9a-hexahydro-5H-cyclopenta[f]quinoline-7-carboxylate (mixture of diastereomers)

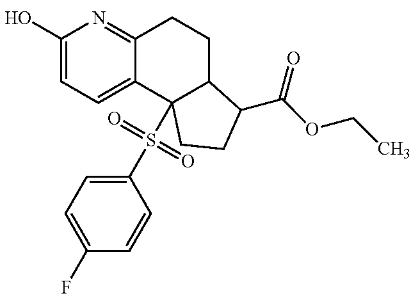 [SMILES: CCOC(=O)C1CCC2(S(=O)(=O)c3ccc(F)cc3)c3ccc(O)nc3CCC12]

A solution of a mixture of diastereomers of ethyl 3-((2,6-dichlorobenzyl)oxy)-9a-((4-fluorophenyl)sulfonyl)-6,6a,7,8,9,9a-hexahydro-5H-cyclopenta[f]quinoline-7-carboxylate (17.0 g, 29.4 mmol) in DCE (147 mL) was treated with HCl (4.0 M in 1,4-dioxane; 44.1 mL, 176 mmol) at rt. The mixture was heated at 50° C. for 18 h, then was concentrated. The residue, a light brown syrup, was dissolved in DCM (20 mL) and added slowly to stirred ether (400 mL). The resulting suspension was stirred for 30 min, and the solid was collected by filtration, washed 3 times with ether, and dried under vacuum to provide a mixture of diastereomers of ethyl 9a-((4-fluorophenyl)sulfonyl)-3-hydroxy-6,6a,7,8,9,9a-hexahydro-5H-cyclopenta[f]quinoline-7-carboxylate (12.3 g). LCMS m/z 420.4 $(M+H)^+$. $^1H$ NMR (499 MHz, MeOH-$d_4$) δ 7.82 (d, J=9.3 Hz, 1H), 7.69-7.63 (m, 2H), 7.35 (t, J=8.8 Hz, 2H), 6.68 (d, J=9.4 Hz, 1H), 4.18 (q, J=7.2 Hz, 2H), 3.20 (td, J=8.4, 5.8 Hz, 1H), 2.97 (ddd, J=13.8, 7.5, 4.4 Hz, 1H), 2.76 (q, J=8.5 Hz, 1H), 2.63-2.55 (m, 1H), 2.24-2.16 (m, 1H), 2.15-2.03 (m, 3H), 2.02-1.94 (m, 1H), 1.62-1.46 (m, 1H), 1.27 (t, J=7.2 Hz, 3H).

Step H: ethyl 9a-((4-fluorophenyl)sulfonyl)-3-(((trifluoromethyl)sulfonyl)oxy)-6,6a,7,8,9,9a-hexahydro-5H-cyclopenta[f]quinoline-7-carboxylate (mixture of diastereomers)

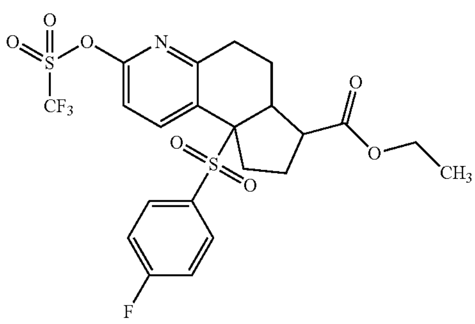 [SMILES: CCOC(=O)C1CCC2(S(=O)(=O)c3ccc(F)cc3)c3ccc(OS(=O)(=O)C(F)(F)F)nc3CCC12]

A solution of a mixture of diastereomers of ethyl 9a-((4-fluorophenyl)sulfonyl)-3-hydroxy-6,6a,7,8,9,9a-hexahydro-5H-cyclopenta[f]quinoline-7-carboxylate (12.3 g, 29.3 mmol) in DCM (147 mL) was treated with pyridine (4.74 mL, 58.6 mmol). The solution was cooled on an ice-water bath and treated dropwise over 30 min with trifluoromethanesulfonic anhydride (7.40 mL, 44.0 mmol). The mixture was stirred at 0-5° C. for 1 h, then treated again with additional pyridine (1.19 mL, 14.7 mmol) and trifluoromethanesulfonic anhydride (1.48 mL, 8.79 mmol). The mixture was stirred at 0-5° C. for 1.5 h, then was treated with saturated aqueous $NH_4Cl$ (2 mL). The mixture was diluted with EtOAc, washed sequentially with water and brine, dried over $Na_2SO_4$, and concentrated to provide a crude mixture of diastereomers of ethyl 9a-((4-fluorophenyl)sulfonyl)-3-(((trifluoromethyl)sulfonyl)oxy)-6,6a,7,8,9,9a-hexahydro-5H-cyclopenta[f]quinoline-7-carboxylate (15.5 g), used without purification. LCMS m/z 552.4 $(M+H)^+$.

Step I: ethyl 3-bromo-9a-((4-fluorophenyl)sulfonyl)-6,6a,7,8,9,9a-hexahydro-5H-cyclopenta[f]quinoline-7-carboxylate (mixture of diastereomers)

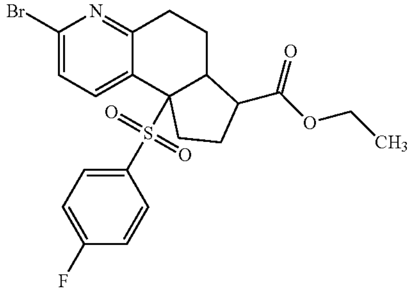 [SMILES: CCOC(=O)C1CCC2(S(=O)(=O)c3ccc(F)cc3)c3ccc(Br)nc3CCC12]

A vigorously stirred solution of a crude mixture of diastereomers of ethyl 9a-((4-fluorophenyl)sulfonyl)-3-(((trifluoromethyl)sulfonyl)oxy)-6,6a,7,8,9,9a-hexahydro-5H-cyclopenta[f]quinoline-7-carboxylate (15.5 g, 28.1 mmol) DCM (20 mL) and toluene (160 mL) was treated with LiBr (11.0 g, 126 mmol), then was treated portionwise with p-toluenesulfonic acid (5.88 g, 30.9 mmol). The mixture was stirred at 50° C. for 16 h, then was cooled to rt and diluted with DCM and water. The organic phase was separated and washed with brine, dried over $Na_2SO_4$, and concentrated. The residue was purified by column chromatography on silica gel (120 g), eluting with EtOAc-hexanes (gradient from 0-30%), to provide a mixture of diastereomers of ethyl 3-bromo-9a-((4-fluorophenyl)sulfonyl)-6,6a,7,8,9,9a-hexahydro-5H-cyclopenta[f]quinoline-7-carboxylate (10.2 g). LCMS m/z 482.4, 484.4 $(M+H)^+$. $^1H$ NMR (499 MHz, $CDCl_3$) δ 7.67 (d, J=8.3 Hz, 1H), 7.43-7.36 (m, 3H), 7.15-7.09 (m, 2H), 4.22 (q, J=7.2 Hz, 2H), 3.30 (td, J=8.8, 5.9 Hz, 1H), 3.21 (ddd, J=13.8, 7.6, 3.2 Hz, 1H), 2.70-2.63 (m, 2H), 2.36 (dtd, J=12.4, 10.0, 7.4 Hz, 1H), 2.17-1.99 (m, 4H), 1.46-1.37 (m, 1H), 1.31 (t, J=7.2 Hz, 3H).

Step J: ethyl 9a-((4-fluorophenyl)sulfonyl)-3-(perfluoropropan-2-yl)-6,6a,7,8,9,9a-hexahydro-5H-cyclopenta[f]quinoline-7-carboxylate (mixture of diastereomers)

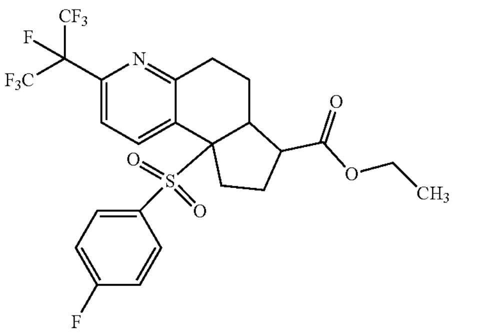 [SMILES: CCOC(=O)C1CCC2(S(=O)(=O)c3ccc(F)cc3)c3ccc(C(F)(C(F)(F)F)C(F)(F)F)nc3CCC12]

Activated copper was prepared by adding zinc dust (24.6 g, 376 mmol) portionwise with stirring to a solution of $CuSO_4$ pentahydrate (45.1 g, 283 mmol) in water (250 mL) over 10 min. The mixture was stirred 10 min longer, then the supernatant was decanted from the red precipitate. This was washed twice with water by decantation, then was stirred with 1 M aqueous HCl (400 mL) for 2.5 h. The supernatant was decanted and the precipitate was washed repeatedly by decantation after stirring with fresh water until the pH of the supernatant was about 7. The solid was stored under water and an inert atmosphere (argon or nitrogen). For use, the solid was washed twice by decantation from MeOH, then twice by decantation from diethyl ether, and dried under vacuum.

A sample of dry activated copper powder (15.8 g, 248 mmol) in a pressure flask was treated with a solution of a mixture of diastereomers of ethyl 3-bromo-9a-((4-fluorophenyl)sulfonyl)-6,6a,7,8,9,9a-hexahydro-5H-cyclopenta[f]quinoline-7-carboxylate (10.2 g, 21.2 mmol) in dry DMF (141 mL). The mixture was flushed with nitrogen for 2 min, then was treated with 1,1,1,2,3,3,3-heptafluoro-2-iodopropane (12.0 mL, 85.0 mmol). The vessel was sealed under nitrogen and heated to 120° C. for 2.5 h. The mixture was cooled to rt, mixed with water (300 mL) and ether (350 mL), and filtered through a Celite pad. The solids were washed 3 times with ether. The combined filtrates were separated and the organic phase was washed sequentially with saturated aqueous $NaHCO_3$, 10% aqueous LiCl and brine, dried over $MgSO_4$, and concentrated to afford a crude mixture of diastereomers of ethyl 9a-((4-fluorophenyl)sulfonyl)-3-(perfluoropropan-2-yl)-6,6a,7,8,9,9a-hexahydro-5H-cyclopenta[f]quinoline-7-carboxylate as a sticky brown solid (12.0 g) which was used without purification. LCMS m/z 572.2 $(M+H)^+$. $^1H$ NMR (499 MHz, $CDCl_3$) δ 8.01 (d, J=8.2 Hz, 1H), 7.60 (dd, J=8.2, 2.6 Hz, 1H), 7.23-7.17 (m, 2H), 7.04-6.98 (m, 2H), 4.28-4.23 (m, 2H), 3.40-3.32 (m, 2H), 2.74-2.63 (m, 2H), 2.53-2.43 (m, 1H), 2.25-2.14 (m, 3H), 1.85-1.77 (m, 2H), 1.33 (t, J=7.2 Hz, 3H).

Step K: 9a-((4-fluorophenyl)sulfonyl)-3-(perfluoropropan-2-yl)-6,6a,7,8,9,9a-hexahydro-5H-cyclopenta[f]quinoline-7-carboxylic acid (mixture of diastereomers)

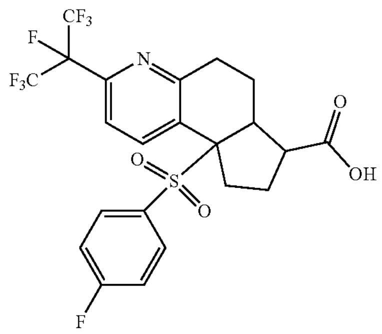 [SMILES: O=C(O)C1CCC2(S(=O)(=O)c3ccc(F)cc3)c3ccc(C(F)(C(F)(F)F)C(F)(F)F)nc3CCC12]

A crude mixture of diastereomers of ethyl 9a-((4-fluorophenyl)sulfonyl)-3-(perfluoropropan-2-yl)-6,6a,7,8,9,9a-hexahydro-5H-cyclopenta[f]quinoline-7-carboxylate (12.0 g, 21.0 mmol) was combined with LiOH monohydrate (3.52 g, 84.0 mmol) in THF-EtOH-water (3:1:1, 175 mL) and stirred at rt for 18 h. The mixture was concentrated under vacuum, and the residue was partitioned between EtOAc (250 mL) and 0.5 M aqueous HCl (181 mL). The organic phase was washed with brine, dried over $MgSO_4$ and concentrated to provide a mixture of diastereomers of 9a-((4-fluorophenyl)sulfonyl)-3-(perfluoropropan-2-yl)-6,6a,7,8,9,9a-hexahydro-5H-cyclopenta[f]quinoline-7-carboxylic acid as light yellow solid (11.4 g). LCMS m/z 544.3 $(M+H)^+$. $^1H$ NMR (499 MHz, DMSO-$d_6$) δ 12.67-12.06 (m, 1H), 8.80 (s, 1H), 7.93 (d, J=8.2 Hz, 1H), 7.77 (dd, J=8.3, 2.9 Hz, 1H), 7.32-7.27 (m, 3H), 3.27-3.20 (m, 1H), 3.05 (ddd, J=14.1, 6.8, 2.2 Hz, 1H), 2.80-2.71 (m, 1H), 2.61 (dt, J=16.4, 3.9 Hz, 1H), 2.30 (s, 1H), 2.20-2.13 (m, 1H), 2.13-1.99 (m, 3H), 1.42 (br s, 1H).

Step L: 2-(trimethylsilyl)ethyl (9a-((4-fluorophenyl)sulfonyl)-3-(perfluoropropan-2-yl)-6,6a,7,8,9,9a-hexahydro-5H-cyclopenta[f]quinolin-7-yl)carbamate (mixture of diastereomers)

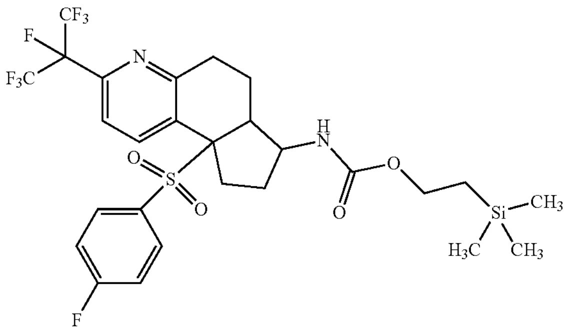 [SMILES: C[Si](C)(C)CCOC(=O)NC1CCC2(S(=O)(=O)c3ccc(F)cc3)c3ccc(C(F)(C(F)(F)F)C(F)(F)F)nc3CCC12]

A suspension of a mixture of diastereomers of 9a-((4-fluorophenyl)sulfonyl)-3-(perfluoropropan-2-yl)-6,6a,7,8,9,9a-hexahydro-5H-cyclopenta[f]quinoline-7-carboxylic acid (11.4 g, 21.0 mmol) in toluene (210 mL) at 0° C. was treated with triethylamine (5.85 mL, 42.0 mmol). The resulting solution was stirred at 0° C. for 5 min, then was treated over 10 min with diphenyl phosphorazidate (10.4 mL, 48.2 mmol). The mixture was stirred for 1 h at 0° C., then warmed to rt and stirred for 2 h more. The mixture was treated with water and extracted with EtOAc. The organic phase was washed with brine, dried over $MgSO_4$ and concentrated. The resulting light yellow oil was treated with 2-(trimethylsilyl)ethan-1-ol (75.0 mL, 524 mmol) and the mixture was heated at 80° C. for 90 min, then was cooled to rt. The mixture was partitioned between water and EtOAc, and the organic phase was washed with brine, dried over $MgSO_4$ and concentrated. The residue was purified by column chromatography on silica gel (220 g), eluting with EtOAc-hexanes (gradient from 0-30%), to provide a mixture of diastereomers of 2-(trimethylsilyl)ethyl (9a-((4-fluorophenyl)sulfonyl)-3-(perfluoropropan-2-yl)-6,6a,7,8,9,9a-hexahydro-5H-cyclopenta[f]quinolin-7-yl)carbamate as a light yellow solid (15.0 g). LCMS m/z 659.3 $(M+H)^+$.

Step M: 2-(trimethylsilyl)ethyl (9a-((4-fluorophenyl)sulfonyl)-3-(perfluoropropan-2-yl)-6,6a,7,8,9,9a-hexahydro-5H-cyclopenta[f]quinolin-7-yl)carbamate, 4 separated diastereomers

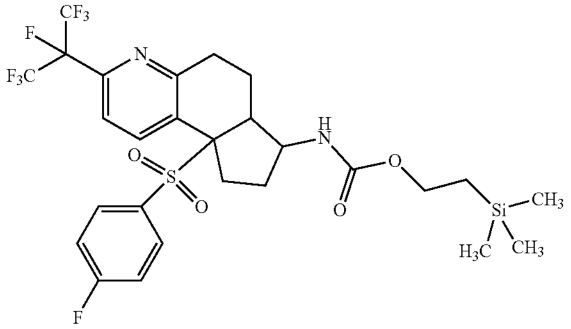 [SMILES: C[Si](C)(C)CCOC(=O)NC1CCC2(S(=O)(=O)c3ccc(F)cc3)c3ccc(C(F)(C(F)(F)F)C(F)(F)F)nc3CCC12]

A sample of a mixture of diastereomers of 2-(trimethylsilyl)ethyl (9a-((4-fluorophenyl)sulfonyl)-3-(perfluoropropan-2-yl)-6,6a,7,8,9,9a-hexahydro-5H-cyclopenta[f]quinolin-7-yl)carbamate (1.2 g) was dissolved in MeOH (17 mL) and separated by SFC (column: Whelko-RR, 5×50 cm, 10 μm (Phenomenex Inc.); pressure 100 bar; temperature 35° C.; mobile phase: $CO_2$-MeOH (85:15); flow rate 300 mL/min; 1 mL injection with 3.5 min cycle time). Three fractions were collected.

The first-eluting fraction was concentrated to provide a single diastereomer of 2-(trimethylsilyl)ethyl (9a-((4-fluorophenyl)sulfonyl)-3-(perfluoropropan-2-yl)-6,6a,7,8,9,9a-hexahydro-5H-cyclopenta[f]quinolin-7-yl)carbamate as a white solid (0.396 g). LCMS m/z 659.0 $(M+H)^+$. $^1H$ NMR (499 MHz, $CDCl_3$) δ 8.09 (d, J=8.2 Hz, 1H), 7.62 (dd, J=8.2, 2.6 Hz, 1H), 7.15-7.08 (m, 2H), 6.97 (t, J=8.5 Hz, 2H), 5.60 (br d, J=8.9 Hz, 1H), 4.25-4.16 (m, 2H), 4.16-4.08 (m, 1H), 3.32 (dt, J=14.2, 7.0 Hz, 1H), 2.75-2.64 (m, 2H), 2.31 (dt, J=14.5, 7.3 Hz, 1H), 2.26-2.19 (m, 1H), 2.18-2.09 (m, 2H), 1.69-1.60 (m, 1H), 1.37 (qd, J=12.8, 3.6 Hz, 1H), 1.07-1.00 (m, 2H), 0.07 (s, 9H).

The second-eluting fraction was concentrated to provide a second single diastereomer of 2-(trimethylsilyl)ethyl (9a-((4-fluorophenyl)sulfonyl)-3-(perfluoropropan-2-yl)-6,6a,7,8,9,9a-hexahydro-5H-cyclopenta[f]quinolin-7-yl)carbamate as a white solid (0.375 g). LCMS m/z 659.0 $(M+H)^+$. $^1H$ NMR (499 MHz, $CDCl_3$) δ 8.09 (d, J=8.2 Hz, 1H), 7.62 (dd, J=8.3, 2.6 Hz, 1H), 7.17-7.08 (m, 2H), 6.97 (t, J=8.5 Hz, 2H), 5.60 (br d, J=8.7 Hz, 1H), 4.26-4.06 (m, 3H), 3.32 (dt, J=14.2, 7.0 Hz, 1H), 2.77-2.60 (m, 2H), 2.31 (dt, J=14.6, 7.4 Hz, 1H), 2.26-2.19 (m, 1H), 2.19-2.07 (m, 2H), 1.70-1.59 (m, 1H), 1.37 (qd, J=12.8, 3.4 Hz, 1H), 1.07-1.00 (m, 2H), 0.07 (s, 9H).

The third-eluting fraction was concentrated, and the residue was dissolved in MeOH (17 mL) and further separated by SFC (column: Cellulose-4, 3×25 cm, 5 μm; pressure 100 bar; temperature 35° C.; mobile phase: $CO_2$-MeOH (85:15) with 0.1% $NH_4OH$; flow rate 180 mL/min; 1 mL injection with 1.1 min cycle time). Two additional fractions were collected.

The first-eluting fraction from the second separation was concentrated to provide a third single diastereomer of 2-(trimethylsilyl)ethyl (9a-((4-fluorophenyl)sulfonyl)-3-(perfluoropropan-2-yl)-6,6a,7,8,9,9a-hexahydro-5H-cyclopenta[f]quinolin-7-yl)carbamate as a white solid (46 mg). LCMS m/z 659.0 $(M+H)^+$. $^1H$ NMR (499 MHz, $CDCl_3$) δ 8.27 (br d, J=8.3 Hz, 1H), 7.66 (dd, J=8.2, 2.5 Hz, 1H), 7.13 (br s, 2H), 6.95 (t, J=8.6 Hz, 2H), 4.68-4.56 (m, 2H), 4.26-4.14 (m, 2H), 3.21 (ddd, J=14.0, 11.0, 8.2 Hz, 1H), 3.12-2.97 (m, 1H), 2.70 (br d, J=16.1 Hz, 1H), 2.44-2.22 (m, 2H), 1.89 (br dd, J=7.9, 3.9 Hz, 1H), 1.72-1.62 (m, 1H), 1.55-1.48 (m, 1H), 1.20-1.08 (m, 1H), 1.05-0.96 (m, 2H), 0.06 (s, 9H).

The second-eluting fraction from the second separation was concentrated to provide a fourth single diastereomer of 2-(trimethylsilyl)ethyl (9a-((4-fluorophenyl)sulfonyl)-3-(perfluoropropan-2-yl)-6,6a,7,8,9,9a-hexahydro-5H-cyclopenta[f]quinolin-7-yl)carbamate as a white solid (46 mg). LCMS m/z 659.0 $(M+H)^+$. $^1H$ NMR (499 MHz, $CDCl_3$) δ 8.27 (br d, J=8.2 Hz, 1H), 7.66 (dd, J=8.3, 2.6 Hz, 1H), 7.14 (br s, 2H), 6.95 (t, J=8.5 Hz, 2H), 4.68-4.56 (m, 2H), 4.30-4.12 (m, 2H), 3.28-3.14 (m, 1H), 3.13-3.00 (m, 1H), 2.70 (br d, J=17.0 Hz, 1H), 2.39-2.23 (m, 2H), 1.89 (br dd, J=8.2, 3.8 Hz, 1H), 1.66 (br dd, J=11.3, 8.7 Hz, 1H), 1.56-1.48 (m, 1H), 1.21-1.08 (m, 1H), 1.00 (br t, J=8.3 Hz, 2H), 0.06 (s, 9H).

Step N: (6aS,7R,9aS)-9a-((4-fluorophenyl)sulfonyl)-3-(perfluoropropan-2-yl)-6,6a,7,8,9,9a-hexahydro-5H-cyclopenta[f]quinolin-7-amine, HCl salt

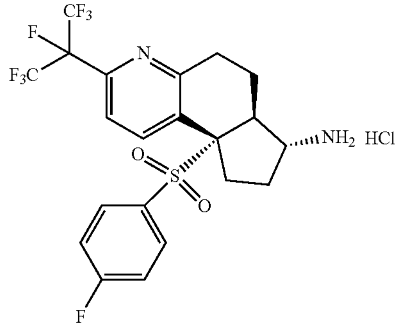 [SMILES: N[C@@H]1CC[C@@]2(S(=O)(=O)c3ccc(F)cc3)c3ccc(C(F)(C(F)(F)F)C(F)(F)F)nc3CC[C@@H]12 ; Cl]

A solution of the second diastereomer of 2-(trimethylsilyl)ethyl (9a-((4-fluorophenyl)sulfonyl)-3-(perfluoropropan-2-yl)-6,6a,7,8,9,9a-hexahydro-5H-cyclopenta[f]quinolin-7-yl)carbamate from Intermediate 1 Step M (0.375 g, 0.569 mmol) in DCE (4.8 mL) was cooled on an ice-water bath and treated with HCl (4.0 M in 1,4-dioxane; 1.42 mL, 5.69 mmol) and the resulting mixture was stirred while heating at 40° C. for 6 h. The mixture was cooled to rt and concentrated to provide (6aS,7R,9aS)-9a-((4-fluorophenyl)sulfonyl)-3-(perfluoropropan-2-yl)-6,6a,7,8,9,9a-hexahydro-5H-cyclopenta[f]quinolin-7-amine, HCl salt, as a white solid (0.33 g). LCMS m/z 514.9 $(M+H)^+$. $^1H$ NMR (499 MHz, MeOH-$d_4$) δ 8.01 (d, J=8.3 Hz, 1H), 7.71 (dd, J=8.2, 2.7 Hz, 1H), 7.31 (dd, J=8.5, 4.9 Hz, 2H), 7.17 (t, J=8.7 Hz, 2H), 3.62-3.52 (m, 1H), 3.37 (dd, J=7.1, 4.8 Hz, 1H), 3.15-3.06 (m, 1H), 2.72 (dt, J=16.7, 3.9 Hz, 1H), 2.46 (ddd, J=14.7, 9.8, 7.3 Hz, 1H), 2.38-2.25 (m, 3H), 2.00 (ddd, J=16.7, 12.9, 3.8 Hz, 1H), 1.53-1.41 (m, 1H). The absolute configuration was determined by single crystal X-ray analysis, from the anomalous dispersion signal using the Flack method (*Acta Cryst. B,* 2013, 69, 249).

Intermediate 2

(S)-2-hydroxy-2-methyl-3-(methylsulfonyl)propanoic acid

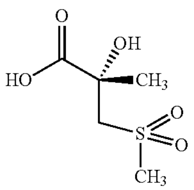

Step A: methyl 2-hydroxy-2-methyl-3-(methylthio)propanoate (racemic)

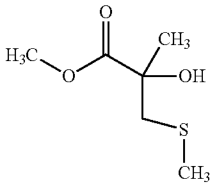

A solution of racemic methyl 2-methyloxirane-2-carboxylate (5.00 g, 42.6 mmol) and acetic acid (3.05 mL, 53.3 mmol) in anhydrous MeOH (125 mL) was stirred under a nitrogen atmosphere on an ice-water bath. When the internal temperature reached about 5° C., the solution was treated portionwise over about 5 min with sodium methanethiolate (11.0 g, 149 mmol), causing an exotherm to about 20° C. After 10 min, the internal temperature was about 12° C., and the cooling bath was removed and stirring was continued. After 2 h from the end of the addition, the mixture was cooled on an ice-water bath and treated with acetic acid (6.1 mL, 107 mmol). The mixture was concentrated under vacuum and the residual sludge was partitioned between ether (300 mL) and water (50 mL). The aqueous phase was extracted twice with ether (2×100 mL), and the combined organic phases were washed sequentially with saturated aqueous $NaHCO_3$ and brine, dried over $Na_2SO_4$ and concentrated under vacuum to give racemic methyl 2-hydroxy-2-methyl-3-(methylthio)propionate as a pale yellow liquid (6.87 g). LCMS m/z 186.9 $(M+Na)^+$. $^1H$ NMR (499 MHz, $CDCl_3$) δ 3.85-3.78 (m, 3H), 3.48 (s, 1H), 2.97 (d, J=14.1 Hz, 1H), 2.77 (d, J=13.9 Hz, 1H), 2.18 (s, 3H), 1.49 (s, 3H).

Step B: methyl 2-hydroxy-2-methyl-3-(methylsulfonyl)propanoate (racemic)

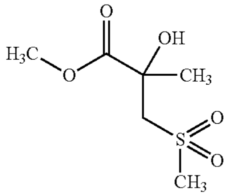

A solution of racemic methyl 2-hydroxy-2-methyl-3-(methylthio)propanoate (8.00 g, 48.7 mmol) in DCM (400 mL) was stirred on an ice-water bath and treated with mCPBA (33.6 g, 146 mmol) in portions over about 5 min. After 5 min more, additional mCPBA (11.2 g, 48.7 mmol) was added. Stirring was continued for 5 min more, then the cooling bath was removed and the white suspension was stirred at rt. After 1.75 h, the mixture was filtered and the white solid was rinsed twice with DCM. The combined filtrates were cooled on an ice-water bath and treated in portions with aqueous $Na_2S_2O_3$ (20 g in 125 mL) and an exotherm was noted. After thorough mixing, the layers were separated and the aqueous phase was extracted with DCM. The combined organic phases were washed sequentially with saturated aqueous $NaHCO_3$ and water, and these two aqueous phases were combined and extracted again with DCM. The combined organic phases were dried over $Na_2SO_4$, filtered and concentrated to provide racemic methyl 2-hydroxy-2-methyl-3-(methylsulfonyl)propanoate as a white solid (6.98 g). LCMS m/z 219.1 $(M+Na)^+$. $^1H$ NMR (499 MHz, $CDCl_3$) δ 3.88 (s, 3H), 3.61 (dd, J=15.1, 1.0 Hz, 1H), 3.44 (d, J=15.0 Hz, 1H), 3.06 (s, 3H), 1.52 (s, 3H).

All of the aqueous phases were combined, treated with solid NaCl and concentrated to a thick sludge. The solid was collected by filtration, and while still damp was stirred with DCM. The mixture was filtered, and the collected solid was rinsed with additional DCM. The layers of the filtrates were separated, the aqueous phase was extracted with DCM, and the combined organic phases were washed with saturated aqueous $NaHCO_3$, dried over $Na_2SO_4$ and concentrated to provide additional racemic methyl 2-hydroxy-2-methyl-3-(methylsulfonyl)propanoate as a light yellow solid (2.23 g).

Step C: methyl (R)-2-hydroxy-2-methyl-3-(methylsulfonyl)propanoate and methyl (S)-2-hydroxy-2-methyl-3-(methylsulfonyl)propanoate

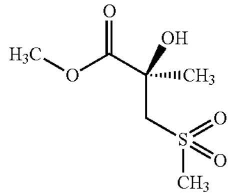

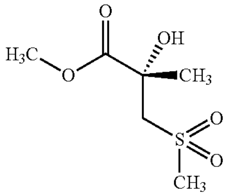

Racemic methyl 2-hydroxy-2-methyl-3-(methylsulfonyl) propanoate (25.3 g) was dissolved in DCM (40 mL) and MeOH (250 mL) and separated by SFC (column: Chiralpak AD-H, 5×25 cm, 5 μm; pressure 100 bar; temperature 40° C.; mobile phase: $CO_2$-MeOH (82:18); flow rate 290 mL/min; 0.7 mL injection with 1.2 min cycle time). Two fractions were collected.

The first-eluting fraction was concentrated to provide methyl (R)-2-hydroxy-2-methyl-3-(methylsulfonyl)propanoate as a white solid (12.3 g). LCMS m/z 197.2 $(M+H)^+$. $^1H$ NMR (499 MHz, $CDCl_3$) δ 3.88 (s, 3H), 3.80 (s, 1H), 3.60 (dd, J=15.1, 1.0 Hz, 1H), 3.43 (d, J=15.0 Hz, 1H), 3.06 (s, 3H), 1.51 (s, 3H).

The second-eluting fraction was concentrated to provide methyl (S)-2-hydroxy-2-methyl-3-(methylsulfonyl)propanoate as a white solid (11.9 mg). LCMS m/z 197.0 $(M+H)^+$. $^1H$ NMR (499 MHz, CHLOROFORM-d) δ 3.88 (s, 3H), 3.80 (s, 1H), 3.60 (dd, J=15.1, 1.0 Hz, 1H), 3.43 (d, J=15.0 Hz, 1H), 3.06 (s, 3H), 1.51 (s, 3H). The absolute configuration of this enantiomer was established by single crystal X-ray analysis of Example 1, from the anomalous dispersion signal using the Flack method.

Step D: (S)-2-hydroxy-2-methyl-3-(methylsulfonyl)propanoic acid

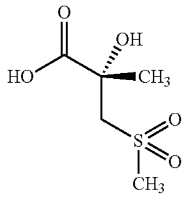

A solution of methyl (S)-2-hydroxy-2-methyl-3-(methylsulfonyl)propanoate (2.00 g, 10.2 mmol) in THF (51 mL) and MeOH (17 mL) was stirred on an ice-water bath and treated with a solution of LiOH hydrate (0.684 g, 16.3 mmol) in water (17 mL). The cooling bath was removed and the slightly cloudy solution was stirred at rt. After 90 min, the mixture was stirred on an ice-water bath and treated with 1 M aqueous HCl (16.3 mL, 16.3 mmol) and concentrated under vacuum to remove the bulk of the organic solvents. The aqueous residue was frozen on dry ice-acetone and lyophilized to provide (S)-2-hydroxy-2-methyl-3-(methylsulfonyl)propanoic acid as a white solid (2.75 g) containing LiCl and residual water, for an estimated purity of 67%. The material was used without further purification. LCMS m/z 181.1 $(M-H)^-$. $^1H$ NMR (499 MHz, DMSO-$d_6$) δ 3.53-3.37 (m, 2H), 3.00 (s, 3H), 1.37 (s, 3H).

Intermediate 3

(R)-2-hydroxy-2-methyl-3-(methylsulfonyl)propanoic acid

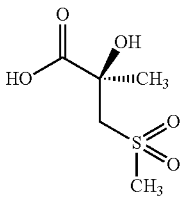

Following the procedure used to prepare Intermediate 2, methyl (R)-2-hydroxy-2-methyl-3-(methylsulfonyl)propanoate (89 mg, 0.454 mmol) was converted to (R)-2-hydroxy-2-methyl-3-(methylsulfonyl)propanoic acid. LCMS m/z 183.0 $(M+H)^+$.

Example 1

(S)—N-((6aS,7R,9aS)-9a-((4-fluorophenyl)sulfonyl)-3-(perfluoropropan-2-yl)-6,6a,7,8,9,9a-hexahydro-5H-cyclopenta[f]quinolin-7-yl)-2-hydroxy-2-methyl-3-(methylsulfonyl)propanamide

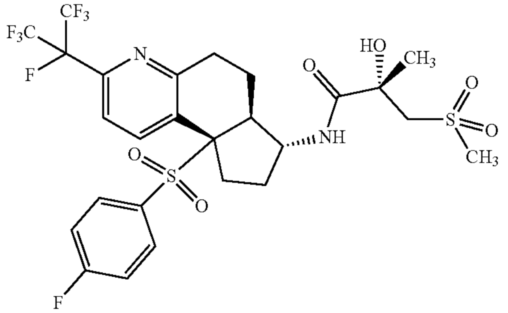 [SMILES: C[C@@](O)(CS(C)(=O)=O)C(=O)N[C@@H]1CC[C@@]2(S(=O)(=O)c3ccc(F)cc3)c3ccc(C(F)(C(F)(F)F)C(F)(F)F)nc3CC[C@@H]12]

A mixture of (6aS,7R,9aS)-9a-((4-fluorophenyl)sulfonyl)-3-(perfluoropropan-2-yl)-6,6a,7,8,9,9a-hexahydro-5H-cyclopenta[f]quinolin-7-amine, HCl salt (Intermediate 1; 9.90 g, 18.0 mmol) in DMF (150 mL) was treated with (S)-2-hydroxy-2-methyl-3-(methylsulfonyl)propanoic acid (Intermediate 2; 6.50 g, 24.3 mmol), HATU (10.6 g, 27.9 mmol) and DIEA (12.6 mL, 71.9 mmol) at 0° C., and the mixture was stirred at rt for 1.5 h. The mixture was cooled on an ice-water bath and treated with water (20 mL). It was partitioned between EtOAc and saturated aqueous $NaHCO_3$ and the organic phase was washed sequentially with 10% aqueous $NaHCO_3$ and brine, dried over $MgSO_4$ and concentrated. The residue was purified by column chromatography on silica gel (220 g), eluting with EtOAc-hexanes (gradient from 0-100%), to provide (S)—N-((6aS,7R,9aS)-9a-((4-fluorophenyl)sulfonyl)-3-(perfluoropropan-2-yl)-6,6a,7,8,9,9a-hexahydro-5H-cyclopenta[f]quinolin-7-yl)-2-hydroxy-2-methyl-3-(methylsulfonyl)propanamide as a white solid (12.0 g). LCMS m/z 679.3 $(M+H)^+$. $^1H$ NMR (499 MHz, MeOH-$d_4$) δ 8.15 (d, J=8.3 Hz, 1H), 7.73 (dd, J=8.3, 2.7 Hz, 1H), 7.34 (dd, J=8.4, 5.1 Hz, 2H), 7.16 (t, J=8.7 Hz, 2H), 4.20-4.09 (m, 1H), 3.66 (d, J=1.0 Hz, 1H), 3.50 (d, J=14.9 Hz, 1H), 3.29-3.21 (m, 1H), 3.12 (s, 3H), 3.07-3.01 (m, 1H), 2.71 (dt, J=16.7, 4.0 Hz, 1H), 2.45 (dt, J=14.0, 6.8 Hz, 1H), 2.26-2.14 (m, 2H), 2.08-1.99 (m, 1H), 1.94 (ddd, J=16.7, 12.3, 4.1 Hz, 1H), 1.55 (s, 3H), 1.49-1.38 (m, 1H). The absolute configuration was determined by single crystal X-ray analysis, from the anomalous dispersion signal using the Flack method.

The following additional examples were prepared using the method of Example 1 from Intermediate 1 and the appropriate carboxylic acid, and were purified by preparative HPLC.
TABLE 1
| Example | Structure | LCMS m/z observed | HPLC $t_R$ (min) |
|---|---|---|---|
| 2 | 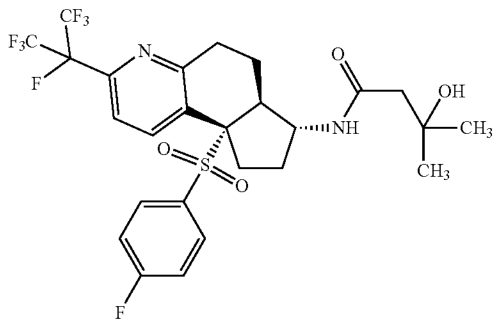 [SMILES: CC(C)(O)CC(=O)N[C@@H]1CC[C@@]2(S(=O)(=O)c3ccc(F)cc3)c3ccc(C(F)(C(F)(F)F)C(F)(F)F)nc3CC[C@@H]12] | 615.2 $(M + H)^+$ | 2.19 |
| 3 | 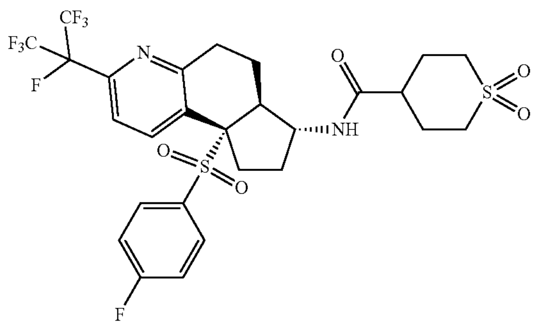 [SMILES: O=C(N[C@@H]1CC[C@@]2(S(=O)(=O)c3ccc(F)cc3)c3ccc(C(F)(C(F)(F)F)C(F)(F)F)nc3CC[C@@H]12)C1CCS(=O)(=O)CC1] | 675.3 $(M + H)^+$ | 2.10 |
| 4 | 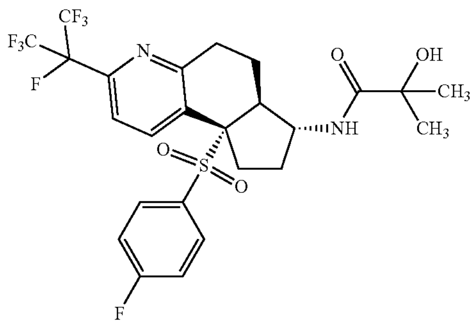 [SMILES: CC(C)(O)C(=O)N[C@@H]1CC[C@@]2(S(=O)(=O)c3ccc(F)cc3)c3ccc(C(F)(C(F)(F)F)C(F)(F)F)nc3CC[C@@H]12] | 601.1 $(M + H)^+$ | 2.09 |
| 5 | 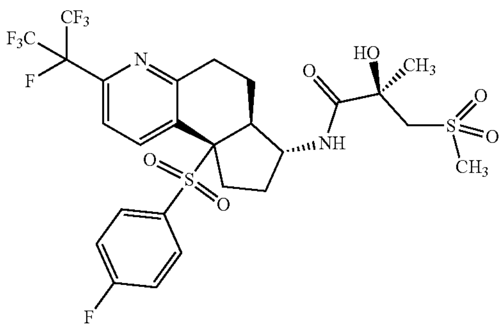 [SMILES: C[C@](O)(CS(C)(=O)=O)C(=O)N[C@@H]1CC[C@@]2(S(=O)(=O)c3ccc(F)cc3)c3ccc(C(F)(C(F)(F)F)C(F)(F)F)nc3CC[C@@H]12] | 679.1 $(M + H)^+$ | 2.09 |

TABLE 1-continued

| Example | Structure | LCMS m/z observed | HPLC $t_R$ (min) |
|---|---|---|---|
| 5 | 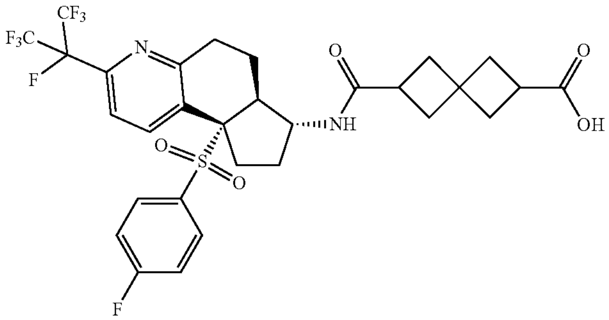 [SMILES: O=C(O)C1CC2(C1)CC(C(=O)N[C@@H]1CC[C@@]3(S(=O)(=O)c4ccc(F)cc4)c4ccc(C(F)(C(F)(F)F)C(F)(F)F)nc4CC[C@@H]13)C2] | 680.9 $(M + H)^+$ | 2.18 |

General RORγ Gal4 Reporter Assay

Inverse agonist activity of potential ligands to RORγ was measured by inhibition of luminescence in a Gal4-luciferase reporter assay in Jurkat cells.

Jurkat cells stably over-expressing the RORγ receptor, Jurkat pEx/Gal/hRORγCLBD/HYG pG5luc/blast, were plated at a concentration of 10,000 cells/well in a 384-well solid white cell culture plate (Perkin Elmer #6007899) in assay buffer RPMI 1640 (Gibco 11875-085 1L) containing 0.1% BSA, 100×HEPES (Gibco 15360-080), 100 mM sodium pyruvate (Gibco 11360-040), 50 mg/mL Hygromycin B (Invitrogen 10687-010) and 10 mg/mL blasticidin (Invitrogen R210-01). 100 nL of test compound in a 3-fold serial dilution, with final concentrations ranging from 40 μM to 0.67 nM, were added to the cells which were then incubated overnight.

The following day, cells were lysed with 10 μL of Steady-Glo Luciferase Assay System (Promega Cat. No. EZ550), and analyzed immediately. $IC_{50}$ values were determined. The $IC_{50}$ value is defined as the concentration of test compound needed to reduce luciferase activity by 50% and is calculated using the four parameter logistic equation to fit the normalized data.

$IC_{50}$ values for compounds of the invention in the RORγ Gal4 reporter assay are provided below.

| Example # | RORγ Gal4, $IC_{50}$ (nm) |
|---|---|
| 1 | 2.5 |
| 2 | 6.0 |
| 3 | 8.4 |
| 4 | 3.9 |
| 5 | 13 |
| 6 | 7.9 |

Human Whole Blood Assay

The compounds were diluted in dimethyl sulfoxide (DMSO) and were transferred to individual wells of a Matrix Technologies clear, V-bottom 384-well plate using the ECHO acoustic liquid handling technology (60 nL per well). Human whole blood samples (30 μL) were added to each well using a CyBio FeliX liquid handling instrument and the plate was shaken on a plate shaker for 3 min, incubating at 37° C. for 1 h. Wells were then treated with CD3+CD28 with a final concentration of 1 μg/mL, 30 μL per well in an AIM-V medium, the plate was shaken on a plate shaker for 3 min before incubating the reaction mixtures at 37° C. for 20 h. Plasma was liberated from each sample by centrifugation (450 g, 5 min, ambient temperature). Treated plasma samples (4 μL) were subsequently transferred to individual wells of a white, shallow, 384-ell ProxiPlate (PerkinElmer) using a FeliX liquid handling instrument and their IL17A content were measured using the AlphaLISA technology as described by the manufacturer, PerkinElmer.

Proprietary BMS data analysis software was used to determine the compound EC50 values where the baseline was established using average DMSO values and 100% induction established using the reference compound values at the highest concentration tested.

Patch Clamp Assay Protocol for Sodium Channel Recording

The cardiac sodium ion channel assay is conducted using human embryonic kidney cells (HEK 293) stably expressing the cloned human sodium channel gene SCN5A ion channel.

The compounds were evaluated at 10 μM in the sodium channel assay, and effects were calculated by measuring inhibition of peak inward currents. Two (2) stimulation frequencies, 1 and 4 Hz (compound A), were used to test for rate-dependent effects of the compound on the sodium channel. All results are reported as mean±SEM. DMSO was used as a vehicle, with the final concentration of DMSO not exceeding 0.1%.

Membrane current recordings were made with a Multiclamp 700 series integrating patch-clamp amplifier (Axon Instruments, Foster City, California) using the whole-cell variant of the conventional patch-clamp technique. Cells expressing sodium SCN5A ion channels were placed in a plexiglass bath chamber, mounted on the stage of an inverted microscope, and perfused continuously with bath solution.

The sodium current bath solution, contained (in mM): 140 NaCl, 4 KCl, 1.8 $CaCl_2$, 1 $MgCl_2$, 10 glucose, 10 HEPES (pH 7.4, NaOH). The patch pipette filling solution used in sodium channel experiments contained (in mM): 130 KCl, 1 $MgCl_2$, 1 $CaCl_2$, 5 ATP-$K_2$, 10 EGTA, 10 HEPES (pH 7.2, KOH).

For determining steady state inhibition, sodium currents were elicited every 5 seconds (0.2 Hz) using the following voltage protocol. Cells were held at a potential of −90 mV and stepped to −20 mV for 45 ms. The peak sodium current in response to the depolarizing step to −20 mV was monitored in the control buffer and after application of test article until a new steady state in the presence of the test article was achieved. To assess the rate dependent inhibition of the sodium currents, trains of voltage steps at frequencies of 1 and 4 Hz (30 sweeps each) were applied to the cell prior to application of test article (control) and after steady state inhibition by test article, as determined at 0.2 Hz frequency. The voltage waveform used in the rate dependence experiments was the same as the waveform used for evaluating steady state inhibition at 0.2 Hz stimulation frequency. Rate dependent inhibition was calculated by comparing the average of the last 3 sweeps of 30 voltage sweeps in presence of test article to the average of the last 3 sweeps of 30 voltage sweeps under control conditions at each frequency tested.

Each compound was tested in 2 cells with 1 HZ stimulation (3 cells with both 1 Hz and 4 Hz stimulations for compound A) at 10 uM concentration except otherwise marked. Currents were sampled at rates at least 2 times the low pass filter rate. The flow rate was kept constant throughout the experiments. All currents were recorded at room temperature ~25° C.

$IC_{50}$ values for Compound 1 and for reference Compound A in the RORγ Gal4 reporter assay, the human whole blood assay and the Na channel assay are provided below.

Compound A is disclosed and claimed in U.S. Pat. No. 9,815,859. Compound 1 has been found to be twice as potent in the human whole blood assay and essentially inactive in the Na channel assay while Compound A has an $IC_{50}$ of 8.6 μM in this assay. These differences make Compound 1 a superior candidate for future development.

| Ex. No. | RORγ Gal4 $IC_{50}$, nM | hWB (nM) | Na Channel (μM) |
|---|---|---|---|
| 1 | 2.5 ± 1.7 nM (n = 8) | 26 ± 13 nM (n = 8) | >30 |
| Compound A | 12 ± 6.4 nM (n = 3) | 52 ± 31 nM (n = 4) | 8.6 |

What is claimed is:

1. The compound of formula (I):

(I)

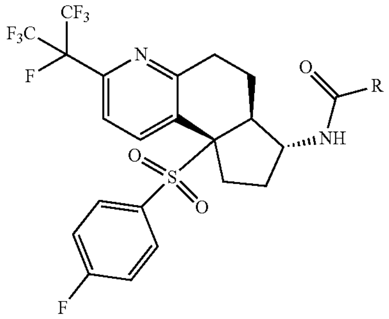

or a pharmaceutically acceptable salt thereof, wherein R is:

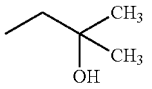
,
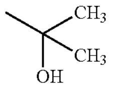
,
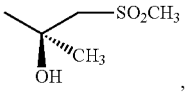
,
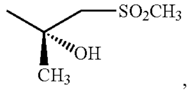
,
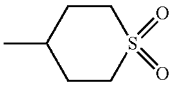
, or
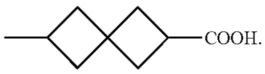

2. The compound of Formula (II)

(II)

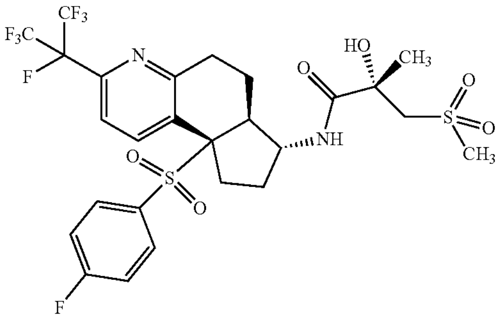

which is (S)—N-((6aS,7R,9aS)-9a-((4-fluorophenyl)sulfonyl)-3-(perfluoropropan-2-yl)-6,6a,7,8,9,9a-hexahydro-5H-cyclopenta[f]quinolin-7-yl)-2-hydroxy-2-methyl-3-(methylsulfonyl) propanamide.

3. A pharmaceutical composition comprising a compound according to claim 1 and a pharmaceutically acceptable carrier or diluent.

4. A pharmaceutical composition comprising a compound according to claim 2 and a pharmaceutically acceptable carrier or diluent.

* * * * *